(12) United States Patent
Martin

(10) Patent No.: US 7,727,973 B2
(45) Date of Patent: Jun. 1, 2010

(54) LIPID A-TYPE COMPOUND AND COMPOSITION CONTAINING IT

(75) Inventor: Richard Martin, Rochecorbon (FR)

(73) Assignee: L'Oreal, Paris (FR)

(*) Notice: Subject to any disclaimer, the term of this patent is extended or adjusted under 35 U.S.C. 154(b) by 796 days.

(21) Appl. No.: 10/972,411

(22) Filed: Oct. 26, 2004

(65) Prior Publication Data

US 2005/0118118 A1 Jun. 2, 2005

Related U.S. Application Data

(60) Provisional application No. 60/528,206, filed on Dec. 10, 2003.

(30) Foreign Application Priority Data

Nov. 6, 2003 (FR) .................................. 03 50798

(51) Int. Cl.
*A61K 31/715* (2006.01)
*A61K 31/7008* (2006.01)
*C07H 5/06* (2006.01)
*C07H 13/00* (2006.01)
*A61K 47/44* (2006.01)

(52) U.S. Cl. .................... 514/53; 514/62; 536/55.2; 536/117; 424/283.1

(58) Field of Classification Search ............ 514/53, 514/62; 536/55.2, 117; 424/283.1
See application file for complete search history.

(56) References Cited

U.S. PATENT DOCUMENTS 5,759,526 A * 6/1998 Simonnet et al. .......... 424/59
5,780,424 A * 7/1998 Pineau et al. ................ 514/2
6,242,229 B1 6/2001 Pineau et al.

FOREIGN PATENT DOCUMENTS

| JP | 07055906 B | * | 6/1995 |
| WO | 97/09032 | | 3/1997 |
| WO | 02/056858 | | 7/2002 |

OTHER PUBLICATIONS

E. Berardesca et al., "Clinical and Instrumental Evaluation of the Activity of an Anti-Wrinkle Cosmetic Product on Cutaneous Relief and Photoaged Skin," J. Appl. Cosmetol. 15, 69-75 (Apr.-Jun. 1997). XP009033298.
Ken-ichi Tanamoto et al., "Endotoxic Properties of Lipid A From Comamonas Testosteroni," Microbiology (2001) 147 (1087-1094). XP-001181665.
Nobuhiko Hasegawa et al., "Elevated Promotion of Prostacyclin Production by Synthetic Lipid A Analogs in Aged Human Endothelial Cells in Culture," Mechanisms of Ageing and Development, Vo. 78, No. 2, (1995) 155-162. XP-001181663.

* cited by examiner

*Primary Examiner*—Shaojia Anna Jiang
*Assistant Examiner*—Everett White
(74) *Attorney, Agent, or Firm*—Oblon, Spivak, McClelland, Maier & Neustadt, L.L.P.

(57) ABSTRACT

Compounds of the formula:

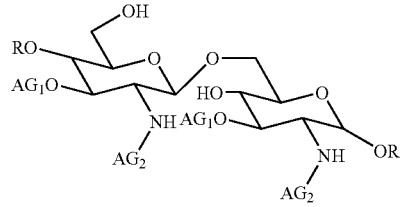

and compositions containing one or more such compounds, the compositions preferably being suitable for topical application to the skin.

11 Claims, 1 Drawing Sheet

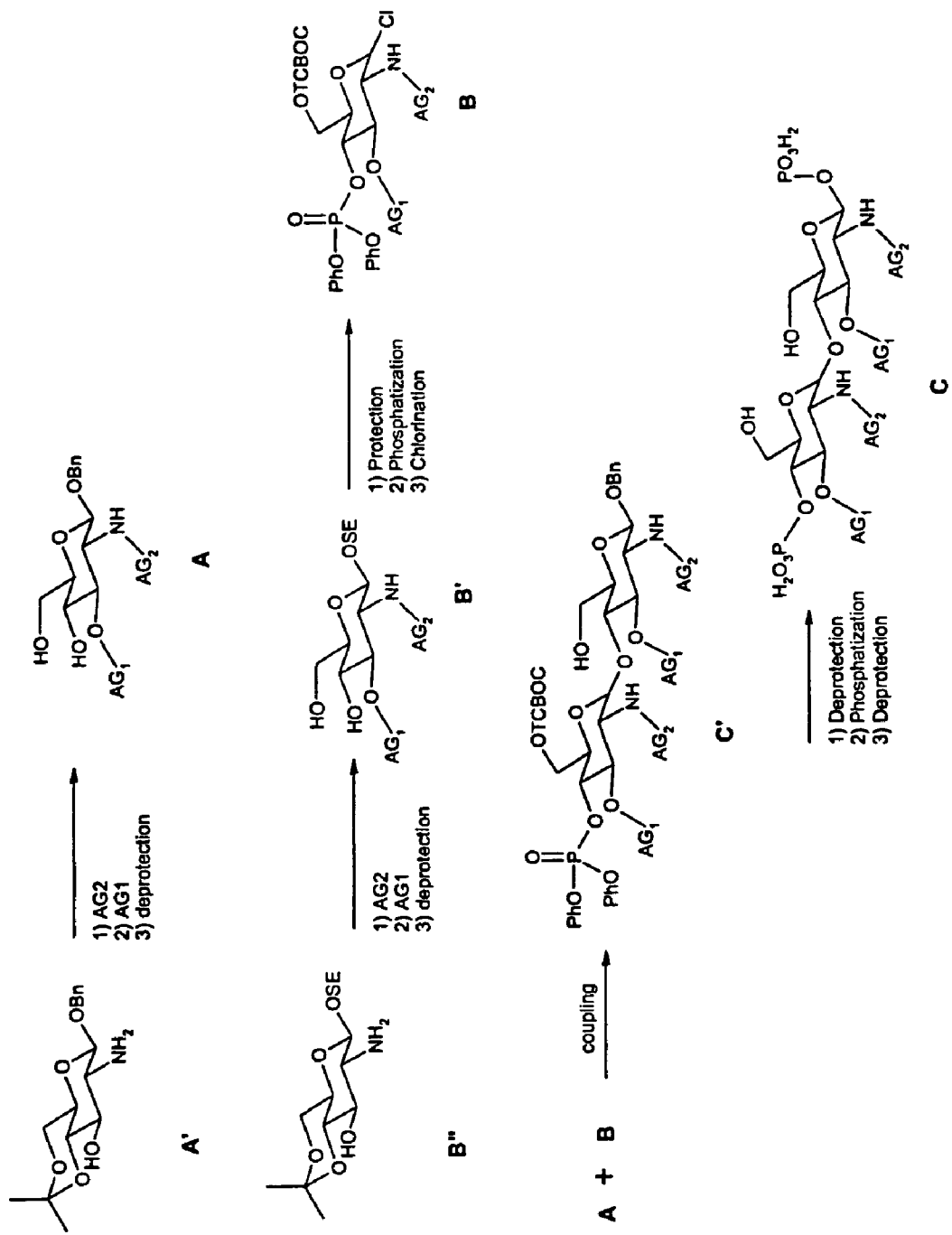

US 7,727,973 B2

LIPID A-TYPE COMPOUND AND COMPOSITION CONTAINING IT

REFERENCE TO PRIOR APPLICATIONS

This application claims priority to U.S. provisional application 60/528,206 filed Dec. 10, 2003, and to French patent application 0350798 filed Nov. 6, 2003, both incorporated herein by reference.

FIELD OF THE INVENTION

The present invention relates to novel compounds of the lipid A type, to compositions comprising at least one such compound, and to its, e.g., cosmetic and dermatological uses.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

The skin constitutes the most important organ of the body and is recognized as one of the main active components of the immune defence system. Three types of epidermal cells participate in this system: the keratinocytes, the melanocytes and the Langerhans' cells. These cells, which are found only in the skin, play a key role in the immune response and in particular in antigen presentation.

Healthy skin is capable of defending itself from external attacks using the means at its disposal. It is known however that the immune system, and more particularly that of the skin, weakens during chronobiological ageing.

In addition, the skin is subjected to constant attack by the environment and by certain chemical products. In particular, the Langerhans' cells are the preferred target for ultraviolet radiation. These attacks result in an immune defence suppressing effect.

This has in particular as consequence a less good destruction of the "sunburn cells" whose accumulation generates cytokines which are themselves capable of generating free radicals and of adversely affecting the dermis (in particular by promoting the degradation of collagen) and the epidermis (in particular by slowing the renewal of the epithelium). These effects contribute towards an acceleration of skin ageing.

An immunostimulatory effect can in this case reestablish the immune functions and more particularly those of the epidermis by strengthening the natural defences of the skin and thus make it possible in particular to combat or prevent the cutaneous signs of ageing.

Bacterial extracts endowed with immunostimulatory properties are known in the prior art. It is moreover known that the lipopolysaccharides (designated hereinafter LPS) anchored in the outer membrane of these bacteria are partly responsible for these properties.

LPSs are complex chemical molecules having a molecular mass of between 8000 and 54 000 daltons, having a stratified structure in three compartments which, from the outside to the inside of the cell, are:

the O antigen, which is a polymer, specific to a given strain, consisting of 1 to 10 units of which each comprises a succession of 5 to 7 sugars, generally amino sugars, the core, which is a polysaccharide which is highly conserved from one bacterial genus to another and which is linked to lipid A by a molecule specific to Gram-negative bacteria, KDO (2-keto-3-deoxyoctulosonic acid), and lipid A which anchors the LPS in the outer membrane of the bacterium.

Lipid A is a dimer of glucosamine carrying, through condensation with its hydroxyl groups situated at the 3- and 3'-positions and with its amino groups situated at the 2- and 2'-positions, more or less unsaturated and hydroxylated fatty acids which may themselves be esterified, on their hydroxyl groups, with other fatty acids. It is these fatty acids which allow anchorage of lipid A in the outer membrane of the cell, which is of a phospholipid nature. In addition, their nature (as $C_{12}$-$C_{18}$) and their position on glucosamines determine the biological activity of the lipids A and therefore of the LPS(s).

The search for biologically active LPSs is however hampered by the problem of the endotoxicity of these molecules. Indeed, most LPSs possess a lipid A which, once unanchored from the cell membrane, is capable of binding to the CD14 receptors and of activating them, thus causing in particular a release of TNF which is capable of causing a septic shock.

Research studies have been carried out in order to determine which structural factors could influence the agonist or antagonist character of the CD14 receptors for these LPSs. It has been demonstrated that the LPSs of cylindrical shape and/or whose fatty acids are arranged symmetrically on the glucosamine backbone are rather antagonists of CD14, in contrast to the conically shaped and/or asymmetric LPSs (Schromm et al, Eur. J. Biochem. 267 pp 2008-2013 (2000)).

BRIEF DESCRIPTION OF THE DRAWING

FIG. 1 describes the synthesis of compounds of formula (I).

SUMMARY OF THE INVENTION

The inventor has now discovered novel lipid A-type compounds endowed with immunostimulatory properties while lacking toxicity. These lipid A-type compounds have a structure comparable to that present in the LPS of *Neisseria meningitidis*, as described in U.S. Pat. No. 6,482,807 (FIG. 4a), without however exhibiting its toxicity.

One lipid A-type compound according to the invention was initially isolated from a strain of *Vitreoscilla filiformis*.

The bacterial strain *Vitreoscilla filiformis* is currently used by L'Oreal for the manufacture of a biomass which is introduced into cosmetic products. The method for preparing this biomass comprise culturing the bacteria in an oxygenated sterile medium, in the presence of mineral salts and sugars; removing and then centrifuging the culture medium comprising the bacteria in order to obtain a biomass which is placed in bottles and then sterilized. The bursting of the cells resulting from the sterilization causes decantation of the biomass into a slurry essentially containing cell membranes and coagulated proteins and containing about 70% of the weight of LPS, and into a supernatant comprising the cytoplasm and containing about 30% of the weight of LPS, the whole bacterium containing (as dry weight) about 10% of LPS. A homogeneous biomass is reconstituted by stirring before use.

Various extracts of *Vitreoscilla filiformis*, endowed with immunostimulatory properties and being nontoxic, have been described by L'Oreal for cosmetic or pharmaceutical use, in particular in the treatment of the cutaneous signs of ageing.

Thus, Application EP-0 765 667 uses a bacterial fraction rich in ribosomes, obtained by centrifugation of the biomass and dialysis of the supernatant obtained. Application EP-0 876 813 additionally describes an immunostimulatory fraction obtained from the culture medium for these bacteria. Finally, Application WO 94/02158 discloses the use, as immunostimulant, of bacterial envelopes or of fractions, in particular of LPS, which are obtained from the said envelopes.

However, the fractions described in the above references only contained a very small quantity if any, undetectable in practice, of free lipid A, whose structure had never been elucidated to date, most if not all of the lipid A being present in the form of LPS itself present in a relatively small quantity in most of the reference extracts, and never being isolated, purified, etc in order to produce a compound in substantially pure form.

In addition, it was not obvious that the immunostimulatory effects of the bacterial fractions of the prior art were linked to the presence of LPS and/or any free lipid A. Indeed, LPS is present in only a small quantity alongside other immunogens which are in particular the murein contained in the cell membranes or the ribosomes present in the cytoplasm (supernatant). In addition, it could have been thought that the heat treatment used to recover these fractions (121° C. for 40 min) had denatured the LPS, thus making it inactive. In particular, it was not predictable that the immunostimulatory effects of the bacterial fractions of the references could be preserved by the LPS which they contained, with no risk of toxicity, after it had been separated from the cell membranes and therefore made potentially active towards the CD14 receptors.

It is therefore surprising that the inventor, having identified the lipid A present in the LPS of *Vitreoscilla filiformis*, has shown that it exhibited an immunostimulatory activity while lacking toxicity. This discovery has allowed the inventor to further develop such compounds and their uses in the cosmetic field where, unlike the pharmaceutical field, active compounds are sought which exhibit perfect tolerance.

Thus, one object of the invention is a substantially pure lipid A-type compound of formula (I):

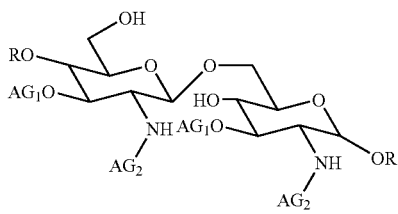

in which:

$AG_1$ denotes a 3-hydroxydecanoyl group $AG_2$ denotes a 3-dodecanoyloxydecanoyl group, R independently denotes a hydrogen atom or a group $PO(OR')_2$, R' independently denoting a hydrogen atom, a saturated or unsaturated, linear or branched $C_1$-$C_6$ alkyl group, or a phenyl or benzyl group, and mixtures thereof. When at least one R denotes a group $PO(OH)_2$ in the formula (I) above, also included within the invention compounds are inorganic salts of such compounds of formula (I), as well as primary, secondary and tertiary amine salts of the compounds of formula (I), as well as phosphoethanolamine salts of the compounds of formula (I).

In the above formula, the term "independently" means that, when more than one of the designated groups is present, they are identical or different from one other. The term "substantially pure" means that the compound is more pure than it is in its natural form, if any, and more pure than any such compound described in EP-0 765 667, EP-0 876 813 and WO 94/02158. In a preferred embodiment the compound is isolated, is preferably not covalently linked to another, and preferably does not form a LPS.

The amine salts of the compounds of formula (I) include the mono-, di- and triethanolamine salts, the mono-, di- or triisopropanolamine salts, 2-amino-2-methyl-1-propanol, 2-amino-2-methyl-1,3-propanediol and tris(hydroxymethyl) aminomethane.

The inorganic salts of the compound of formula (I) include sodium, magnesium, potassium, zinc and calcium salts.

Another subject of the invention is a composition, preferably one suitable for topical application to the skin, containing, preferably in a cosmetically acceptable medium, at least one such compound of formula (I).

The expression "cosmetically acceptable" is understood to mean, for the purposes of the present invention, an inert medium which does not cause itching, tingling or red blotches which can put off the user of the composition, and which has a pleasant appearance, odour and feel.

A further subject of the present invention is the cosmetic use of at least one compound of formula (I) as defined above, or of the abovementioned composition, for skin care, in particular to prevent or treat the cutaneous signs of ageing and/or to protect the skin against the damaging effects of UV radiation.

A further subject of the present invention is the cosmetic treatment of the skin, comprising the topical application of the abovementioned compound or composition to the skin. This method is in particular intended to prevent or treat the cutaneous signs of ageing and/or to protect the skin against the damaging effects of UV radiation.

A further subject of the present invention is the use of at least one compound of formula (I) as defined above, or of the abovementioned composition, for the preparation of a dermatological composition intended to strengthen the cutaneous immune defences.

The compounds of formula (I) can be prepared by chemical synthesis, for example according to the method illustrated in the accompanying figure and described in greater detail in Example 1 below. As a variant, some compounds of formula (I) may be obtained from a culture of nonfruiting, nonphotosynthetic filamentous bacteria.

In this latter variant of the method, it is possible to use a culture of bacteria of the order Beggiatoales, for example of the genus *Beggiatoa*, such as the various strains of *Beggiatoa alba* according to the definition given in Arch. Microbiol. (1984) 137, 139-144. It is also possible to use a culture of bacteria of the genus *Vitreoscilla, Flexithrix* or *Leucothrix*. These bacteria are found in water or the sea or in some thermal springs.

Among the bacteria which can be used, those which are particularly useful include:

*Vitreoscilla beggiatoides* (ATCC 43181)
*Vitreoscilla stercoraria* (ATCC 15218)
*Vitreoscilla beggiatoides* (ATCC 43181)
*Beggiatoa alba* (ATCC 33555)
*Flexithrix dorothaea* (ATCC 23163)
*Leucothrix mucor* (ATCC 25107)

These bacteria may be cultured according to known methods, as described for example in Application WO 94/02158, in order to obtain a biomass which can be separated and isolated in various ways, for example by filtration or centrifugation. A lipopolysaccharide fraction is then extracted from this biomass, for example according to the so-called Westphal method (Westphal, O. and Jann, K. (1965), in R. L. Whistler (ed.) Methods in Carbohydrate Chemistry Vol. 5, Academic Press, New York, pp. 83-91). This method comprises an extraction with the aid of phenol-water mixtures at 65° C. followed by dialysis in order to remove the phenol. A bacterial fraction with a high concentration of LPS is thus obtained. Compounds of formula (I) according to the invention may then be obtained from this fraction, for example according to one of the methods described in Morrison, D. C. and Leive, L. (1975) J. Biol. Chem. 250, 2911-2919 or Takayama, K. et al. (1981) Cancer Research 41, 2654-2657.

The composition according to the present invention preferably contains a sufficient quantity of at least one compound of formula (I) so as to obtain the desired effect, and preferably from 0.01 to 0.1% by weight of this compound(s), relative to the total weight of the composition.

The composition according to the invention may be provided in any form, including any of the galenic forms conventionally used for topical application and in particular in the form of aqueous gels or aqueous or aqueous-alcoholic solutions. It may also, upon addition of a fatty or oily phase, be provided in the form of dispersions of the lotion or serum type, of emulsions having a liquid or semiliquid consistency of the milk type, which are obtained by dispersing a fatty phase in an aqueous phase (O/W) or conversely (W/O), or of suspensions or emulsions having a soft, semisolid or solid consistency of the cream or gel type, or alternatively of multiple emulsions (W/O/W or O/W/O), of microemulsions, vesicular dispersions of the ionic and/or nonionic type, or wax/aqueous phase dispersions. These compositions are prepared according to the customary methods.

According to a preferred embodiment of the invention, the composition is provided in the form of an emulsion.

The composition used according to the invention may be fluid to a greater or lesser degree and may have the appearance of a white or coloured cream, an ointment, a milk, a lotion, a serum, a paste or a foam. It may be optionally applied to the contour of the eye in solid form, and for example in a form cast in a dish or in stick form.

When the composition is in the form of an emulsion, the proportion of the oily phase of the emulsion may range for example from 5 to 80% by weight, and preferably from 5 to 50% by weight relative to the total weight of the composition. The oils, emulsifiers and coemulsifiers used in the composition in the form of an emulsion are chosen from those conventionally used in the cosmetic or dermatological field. The emulsifier and coemulsifier are generally present in the composition in a proportion ranging from 0.3 to 30% by weight, and preferably from 0.5 to 20% by weight relative to the total weight of the composition. The emulsion may additionally contain lipid vesicles.

Useful fatty substances which can be used in the invention include oils and in particular mineral oils (liquid paraffin), oils of plant origin (avocado oil, soyabean oil), oils of animal origin (lanolin), synthetic oils (perhydrosqualene), silicone oils (cyclomethicone) and fluorinated oils (perfluoropolyethers). It is also possible to use, as fatty substances, fatty alcohols such as cetyl alcohol, fatty acids, waxes and gums and in particular silicone gums.

Useful emulsifiers and coemulsifiers which can be used in the invention include for example fatty acid esters of polyethylene glycol such as PEG-100 stearate, PEG-50 stearate and PEG-40 stearate; fatty acid esters of polyols such as glyceryl stearate, sorbitan tristearate and the oxyethylenated sorbitan stearates available under the trade names Tween® 20 or Tween® 60, for example; and mixtures thereof.

The composition according to the invention may also contain adjuvants useful for example in the cosmetic and dermatological fields, such as hydrophilic or lipophilic gelling agents, active agents, screening agents, preservatives, solvents, perfumes, fillers, pigments, odour absorbers and colouring matter. The quantities of these various adjuvants are those used in the fields considered, and are for example from 0.01 to 20% of the total weight of the composition. These adjuvants, depending on their nature, may be introduced into the fatty phase or into the aqueous phase. These adjuvants, and their concentrations, should be such that they do not adversely affect the advantageous properties according to the invention.

Useful hydrophilic gelling agents include in particular carboxyvinyl polymers (carbomer), acrylic copolymers such as acrylate/alkyl acrylate copolymers, polyacrylamides, polysaccharides, natural gums and clays, and, as lipophilic gelling agents, there may be mentioned modified clays such as bentones, metal salts of fatty acids and hydrophobic silica.

Useful active agents include: desquamating or moisturizing agents; depigmenting agents; antiglycation agents; NO-synthase inhibitors, agents stimulating the synthesis of dermal or epidermal macromolecules and/or preventing their degradation; agents stimulating the proliferation of fibroblasts or keratinocytes and/or the differentiation of keratinocytes; tightening agents; antipollution and/or anti-free radical agents; and muscle-relaxing or skin-relaxing agents.

Examples of preferred active agents for use in the present invention include: (N-2-hydroxyethylpiperazine-N-2-ethane)sulphonic acid (HEPES); 2-oxothiazolidine-4-carboxylic acid (procysteine); $\alpha$- and $\beta$-hydroxy acids, in particular 5-(n-octanoyl)salicyclic acid; ceramides; sapogenins and plant extracts, in particular extracts of Wild Yam, containing it; resveratrol; ascorbic acid and its derivatives; retinoids and carotenoids, in particular retinol, retinyl esters and lycopene; pseudodipeptides such as {2-[acetyl-(3-trifluoromethylphenyl)amino]-3-methylbutyrylamine}acetic acid; soyabean extracts, in particular soyabean protein hydrolysates or soyabean extracts rich in isoflavones; tocopherol and its esters; and mixtures thereof.

As screening agents which can be used in the present invention, there may be mentioned organic or inorganic photoprotective agents, agents which are active in UVA and/or UVB, and which are fat-soluble, water-soluble or which are insoluble in cosmetic solvents.

Useful organic photoprotective agents include, in particular, anthranilates; cinnamic derivatives; dibenzoylmethane derivatives; salicylic derivatives, camphor derivatives; triazine derivatives such as those described in U.S. Pat. No. 4,367,390, EP 863145, EP 517104, EP 570838, EP 796851, EP 775698, EP 878469, EP 933376, EP 507691, EP 507692, EP 790243 and EP 944624; benzophenone derivatives; $\beta,\beta$-diphenyl acrylate derivatives; benzotriazole derivatives; benzalmalonate derivatives; benzimidazole derivatives; imidazolines; bis-benzoazolyl derivatives as described in Patents EP 669323 and U.S. Pat. No. 2,463,264; p-aminobenzoic acid (PABA) derivatives; methylenebis(hydroxyphenylbenzotriazole) derivatives as described in Applications U.S. Pat. No. 5,237,071, U.S. Pat. No. 5,166,355, GB 2303549, DE 19726184 and EP 893119; screening polymers and screening silicones such as those described in particular in Application WO 93/04665; dimers derived from $\alpha$-alkylstyrene such as those described in Patent Application DE 19855649; 4,4-diarylbutadienes such as those described in Applications EP 0967200, DE 19746654, DE 19755649, EP-A-1008586, EP 1133980 and EP 133981 and mixtures thereof.

Useful photoprotective agents which are active in UV-A and/or UV-B include those designated below under their INCI name:

para-aminobenzoic acid derivatives, including the following: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicylic derivatives, including the following: Homosalate sold in particular under the name "NEO HELIOPAN OS" by HAARMANN and REIMER, Dipropyleneglycol Salicylate sold in particular under the name "DIPSAL" by SCHER, TEA Salicylate, sold in particular under the name "NEO HELIOPAN TS" by HAARMANN and REIMER, dibenzoylmethane derivatives, including the following: Butyl Methoxydibenzoylmethane sold in particular under the trade name "PARSOL 1789" by HOFFMANN LA ROCHE, Isopropyl Dibenzoylmethane, cinnamic derivatives, including the following: Ethylhexyl Methoxycinnamate sold in particular under the trade name "PARSOL MCX" by HOFFMANN LA ROCHE, Isopropyl Methoxy cinnamate, Isoamyl Methoxy cinnamate sold in particular under the trade name "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, β,β'-diphenyl acrylate derivatives, including the following: Octocrylene sold in particular under the trade name "UVINUL N539" by BASF, Etocrylene, sold in particular under the trade name "UVINUL N35" by BASF, benzophenone derivatives, including the following: Benzophenone-1 sold in particular under the trade name "UVINUL 400" by BASF, Benzophenone-2 sold in particular under the trade name "UVINUL D50" by BASF, Benzophenone-3 or Oxybenzone, sold in particular under the trade name "UVINUL M40" by BASF, Benzophenone-4 sold in particular under the trade name "UVINUL MS40" by BASF, Benzophenone-5, Benzophenone-6 sold in particular under the trade name "HELISORB 11" by NORQUAY, Benzophenone-8 sold in particular under the trade name "SPECTRA-SORB UV-24" by AMERICAN CYANAMID, Benzophenone-9 sold in particular under the trade name "UVINUL DS-49" by BASF, Benzophenone-12, and n-hexyl 2-(4-diethylamino-2-hydroxybenzoyl)benzoate, benzylidenecamphor derivatives, including the following: 3-Benzylidene camphor, 4-Methylbenzylidene camphor sold in particular under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, benzimidazole derivatives, including the following: Phenylbenzimidazole Sulphonic Acid sold in particular under the trade name "EUSOLEX 232" by MERCK, Disodium Phenyl Dibenzimidazole Tetra-sulphonate sold in particular under the trade name "NEO HELIOPAN AP" by HAARMANN and REIMER, triazine derivatives, including the following: Anisotriazine sold in particular under the trade name "TINOSORB S" by CIBA SPECIALTY CHEMICALS, Ethylhexyl triazone sold in particular under the trade name "UVINUL T150" by BASF, Diethylhexyl Butamido Triazone sold in particular under the trade name "UVASORB HEB" by SIGMA 3V, and 2,4,6-tris(diisobutyl 4'-aminobenzalmalonate)-s-triazine, benzotriazole derivatives, including the following: Drometrizole Trisiloxane sold under the name "SILATRIZOLE" by RHODIA CHIMIE, Methylene bis-Benzotriazolyl Tetramethylbutylphenol, sold in particular in solid form under the trade name "MIXXIM BB/100" by FAIRMOUNT CHEMICAL or in micronized form in aqueous dispersion under the trade name "TINOSORB M" by CIBA SPECIALTY CHEMICALS, anthranilic derivatives, including Menthyl anthranilate sold under the trade name "NEO HELIOPAN MA" by HAARMANN and REIMER, imidazoline derivatives, including Ethylhexyl Dimethoxybenzylidene Dioxoimidazoline Propionate.

There may also be mentioned the benzalmalonate derivatives, including the polyorganosiloxane containing benzalmalonate functional groups sold under the trade name "PARSOL SLX" by HOFFMANN LAROCHE, and the 4,4-diarylbutadiene derivatives, including the 1,1-dicarboxy(2,2'-dimethylpropyl)-4,4-diphenylbutadiene.

The organic photoprotective agents most particularly preferred are chosen from the following compounds: Ethylhexyl Salicylate, Ethylhexyl Methoxycinnamate, Octocrylene, Phenylbenzimidazole Sulphonic Acid, Benzophenone-3, Benzophenone-4, Benzophenone-5, 4-Methylbenzylidene camphor, Terephthalylidene Dicamphor Sulphonic Acid, Disodium Phenyl Dibenzimidazole Tetra-sulphonate, 2,4,6-tris(diisobutyl 4'-aminobenzalmalonate)-s-triazine, Anisotriazine, Ethylhexyl triazone, Diethylhexyl Butamido Triazone, Methylene bis-Benzotriazolyl Tetramethylbutylphenol, Drometrizole Trisiloxane, 1,1-dicarboxy(2,2'-dimethylpropyl)-4,4-diphenylbutadiene and mixtures thereof.

Preferred inorganic photoprotective agents include pigments or alternatively nanopigments (mean primary particle size: generally between 5 nm and 100 nm, preferably between 10 nm and 590 nm) of metal oxides, coated or otherwise, such as for example nanopigments of titanium oxide (amorphous or crystallized in rutile and/or anatase form), of iron oxide, of zinc oxide, of zirconium oxide or of cerium oxide which are all UV photoprotective agents well known per se. Conventional coating agents are moreover alumina and/or aluminium stearate. Such coated or uncoated nanopigments of metal oxides are described in particular in Patent Applications EP518772 and EP518773.

The screening agents can be used in any amount and may generally be present in the compositions according to the invention in proportions ranging from 0.1 to 20% by weight relative to the total weight of the composition, and preferably ranging from 0.2 to 15% by weight relative to the total weight of the composition.

The invention will now be illustrated by the following nonlimiting examples. In these examples, the quantities are indicated as a percentage by weight. The constituents of the compositions are designated according to the CTFA nomenclature.

EXAMPLES

Example 1

Preparation of Compound 1 a) Synthesis of A

A solution containing commercial glucosamine A' (1.4 mmol) and 3-dodecanoyloxydecanoyl (1.54 mmol) in $CH_2Cl_2$ (15 ml) are treated with EDC.MeI (2.10 mmol) with stirring at room temperature overnight. The reaction mixture is then concentrated and the residue is purified by flash chromatography on silica gel.

The preceding compound (15.2 mmol) is dissolved with 3-hydroxydecanoyl (16.7 mmol) and 4-pyrrolidinopyridine (1.7 mmol) in $CH_2Cl_2$ (95 ml). EDC.MeI (16.7 mmol) is added and the medium is stirred at room temperature overnight. The reaction mixture is then concentrated and the residue is purified by flash chromatography on silica gel.

The acetonide from above is dissolved in an acetic acid/water (4/1) mixture and is heated at 60° C. for 1 h. The medium is then concentrated and purified by flash chromatography on silica gel to give the intermediate A.

b) Synthesis of B

B' is obtained from the commercial product B" by applying the same protocol used for the synthesis of A (see above).

TCBOC-Cl (13.2 mmol) in $CH_2Cl_2$ (25 ml) is added dropwise over 15 min to a solution at 0° C. containing B' (12 mmol) and pyridine (25 mmol) in $CH_2Cl_2$ (125 ml). The mixture is then gently brought to room temperature over 3.5 h. 4-Pyrrolidinopyridine (6.0 mmol), N,N-diisopropylethylamine (60 mmol) and diphenyl chlorophosphonate (18 mmol) are added successively. The mixture is stirred at room temperature for 5 h. The reaction is then diluted with $CH_2Cl_2$, washed with a cold aqueous HCl solution (7.5%) and then with a saturated aqueous $NaHCO_3$ solution, and then dried and concentrated. The residue is purified by flash chromatography on silica gel.

$ZnCl_2$ (1.0 M in ether, 2.41 mmol) is added at 0° C. to a solution containing the compound obtained above (4.84 mmol) and dichloromethyl methyl ether (24.2 mmol) in $CHCl_3$ (60 ml). The mixture is gently brought to room temperature, and then is stirred at room temperature overnight. The reaction medium is then diluted with EtOAc, washed with a saturated aqueous $NaHCO_3$ solution and dried and concentrated. The residue is purified by flash chromatography on silica gel to give compound B.

c) Synthesis of Compound 1

A solution containing B (1.85 mmol) and A (1.54 mmol) in 1,2-dichloroethane (18.5 mmol) is stirred with 4 Å molecular sieve (1 g) for 1 h, and treated with AgOTf (5.55 mmol) in a single portion. After stirring for 4 h at room temperature in the dark, additional AgOTf (1.85 mmol) is added and the reaction is stirred overnight. The creamy mixture is then filtered on Celite and concentrated. Purification by flash chromatography on silica gel provides compound C'.

A solution containing C' (0.46 mmol) in an AcOH (4.5 ml)/THF (40 ml) mixture is hydrogenated in the presence of $PtO_2$ (0.45 g) at room temperature at a pressure of 70 psig for 18 h. The solution is diluted with $CHCl_3$/MeOH (2/1), and then briefly sonicated. The catalyst is then filtered and washed with the $CHCl_3$/MeOH (2/1) mixture. The filtrates are grouped together and concentrated. The residue is purified by flash chromatography on silica gel.

The preceding product (12 mmol) in $CH_2Cl_2$ (25 ml) is stirred in the presence of N,N-diisopropylethylamine (60 mmol) and $POCl_3$ (18 mmol) at room temperature for 5 h. The reaction is then concentrated. The reaction medium is then diluted with $CH_2Cl_2$, washed with a saturated aqueous $NaHCO_3$ solution, and then dried and concentrated. The residue is then dissolved in acetic acid (100 ml) and heated to 60° C. with zinc dust (0.9 ml). The reaction is then cooled and filtered on Celite, and concentrated. Purification by flash chromatography on silica gel provides compound 1.

Example 2

Demonstration of the Immunostimulatory Effect

The immunostimulatory effect was evaluated on a *Vitreoscilla filiformis* fraction rich in LPS in which the lipid A is a compound of formula (I) in accordance with the present invention.

a) Extraction of the LPS

A strain of *Vitreoscilla filiformis* (ATCC 15551) was cultured according to the technique described in WO-94/02158. Culturing was carried out at 26 C. for at least 48 hours until a suitable cell concentration corresponding to an optical density at 600 nm of greater than or equal to 1.5 was obtained. The strain was subcultured at 2% V/V in fresh medium every 48 hours until a stable culture was obtained. A 1 liter conical flask containing 200 ml of fresh medium was then inoculated with 4 ml of the above culture.

Culturing in the conical flask was carried out at 26 C. on a culture table agitated at 100 revolutions/minute. The base stock thus obtained served as inoculum for a 10 l fermenter. Growth occurred at 26 C., pH 7, 100 revolutions/minute and $pO_2$ greater than or equal to 15%.

After 48 hours of growth, the biomass was transferred into a fermenter with a working capacity of 600 liters, in order to be cultured under the same conditions. The following Table I culture medium was employed:

TABLE I

| COMPOSITION | CONCENTRATION |
| --- | --- |
| Autolytic extract of Biokar yeast (Ref. 112002) | 2.0 g/l |
| Soybean papain peptone (from PPS-USP Biokar Ref. 1 1601) | 2.0 g/l |
| Heller microelements | 2.0 ml/l |
| Anhydrous glucose | 2.0 g/l |
| $CaCl_2 \cdot 10H_2O$ | 0.066 g/l |
| Distilled water | 100.0 ml |

The pH was adjusted to 7.15 by addition of 1N sodium hydroxide or potassium hydroxide before sterilization at 121 C. for 20 min.

The composition of the Heller microelements, per 1 l of distilled water, was as shown in Table II:

TABLE II

| | |
| --- | --- |
| $ZnSO_4 \cdot 7H_2O$ | 1 g |
| $MnSO_4 \cdot H_2O$ | 0.076 g |
| $CuSO_4 \cdot 5H_2O$ | 0.003 g |
| KI | 0.010 g |
| $H_3BO_3$ | 1 g |

TABLE II-continued

| | |
|---|---|
| $AlCl_3 \cdot 6H_2O$ | 0.050 g |
| $NiCl_2 \cdot 6H_2O$ | 0.030 g |

0.2 g/l of a polymethylsiloxane-type antifoaming agent (Silbione 97350 RP) was added to this culture medium. The temperature was adjusted to between 26 and 30 C., the optimum being 29 C.

A complete growth cycle required about 48 h.

Aeration was regulated by a mass flow meter in order to provide a minimum of 20% dissolved oxygen.

There was virtually no residual glucose at the end of the growth.

The biomass was separated by centrifugation.

This was carried out in an industrial-type centrifuge cooled to 4 C., making it possible to obtain a separating power equivalent to 8000×g, run for 2 minutes.

The culture medium thus harvested could then be stored by freezing for use at a later date.

The freezed product was defreezed at 4° C., then the cells were put into 1 or 2 liter packagings that were thus autoclaved for 20-40 minutes at 121° C.

420 ml of autoclaved product was centrifuged at 100 000 g 4° C. for 1 h 30 min. The pellets were recovered and then resuspended in 150 ml of solubilization buffer. After heating at 100° C. for 1 hour, centrifugation was carried out at 10 000 g 4° C. for 30 minutes. 100 ml of the supernatant was removed to which were added 60 mg of proteinase K (0.6 mg/ml). After heating at 60° C. for one hour, 200 ml of a magnesium chloride solution in ethanol were added and the composition obtained was kept at −20° C. overnight. Two precipitations with ethanol were then carried out at −20° C. After resuspending in distilled water, the product obtained was dialysed against water and then freeze-dried.

b) Expression of the Molecules at the Surface of Langerhans' Cells

Normal human Langerhans' cells, obtained by enzymatic treatment, were incubated for 18 hours with 100 μg/ml of the product obtained in step (a) above or 100 μg/ml of E. coli LPS, used as positive control.

The experiment was repeated three times.

The expression of the HLA-DR molecule was expressed in the form of ratio of mean intensity of fluorescence. Its mean, for the three experiments, was 1.28 for the product tested, not significantly different from that measured for the reference LPS (1.19).

In addition, the expression of the B7-2 molecules, assessed by electron microscopy and expressed by the number of gold grains per 100 μm of membrane, is much higher when the cells are incubated with the product tested (162.4±13.7) than with the reference LPS (88.5±8.3).

Finally, the capacity for phagocytosis of latex beads by the Langerhans' cells expressed as number of phagocytosed beads per 100 μm² of membrane, is significantly increased in the presence of the product tested (54.1±11.4) and greater than that which is obtained in the presence of the reference LPS (34.7±6.9).

Conclusion:

The product tested induces, at the surface of Langerhans' cells, an increase in the expression of the principal molecules involved in the contact with the T lymphocytes, which is necessary for initiating the immune response. In addition, phagocytosis being one of the first stages of the functional activity of the Langerhans' cells in providing the body's defence against bacterial or viral pathogenic agents, its stimulation by the LPS tested suggests an increased activity of elimination of pathogenic agents by the Langerhans' cells which can be attributed to the lipid A of this LPS.

Example 3

Cosmetic Composition

An O/W emulsion is prepared from the following ingredients, in the proportions by weight indicated below:

| | |
|---|---|
| Glyceryl stearate | 2.0% |
| Polysorbate 60 | 2.0% |
| Stearic acid | 1.5% |
| Sodium hydroxide | 0.7% |
| Carbomer | 0.4% |
| Sunflower oil | 15.0% |
| Propylene glycol | 3.0% |
| Preservatives | 0.5% |
| Compound 1* | 0.1% |
| Water | qs 100% |

*obtained as described in Example 1

This composition may be prepared in a conventional manner by a person skilled in the art. Its method of preparation preferably comprises a step of dissolving compound 1 in an aqueous sodium hydroxide solution. The above written description of the invention provides a manner and process of making and using it such that any person skilled in this art is enabled to make and use the same, this enablement being provided in particular for the subject matter of the appended claims, which make up a part of the original description and including a substantially pure compound of formula (I):

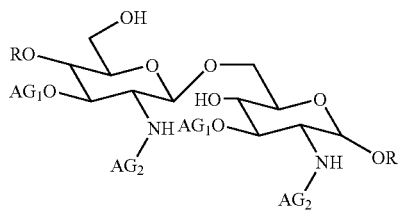

in which:

$AG_1$ denotes a 3-hydroxydecanoyl group $AG_2$ denotes a 3-dodecanoyloxydecanoyl group, where R denotes a hydrogen atom or a group $PO(OR')_2$, R' denoting a hydrogen atom, a saturated or unsaturated, linear or branched $C_1$-$C_6$ alkyl group, or a phenyl or benzyl group, wherein in the case where R denotes a group $PO(OH)_2$ in formula (I) above, an inorganic salt of the compound of formula (I), or a primary, secondary or tertiary amine salt of the compound of formula (I), or a phosphoethanolamine salt of the compound of formula (I) are also included, and mixtures thereof, it being understood that groups R and R' are identical or different from each other when two or more of each are present.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method to protect the skin against the damaging effects of UV radiation, the method comprising applying to skin in need thereof an effective amount of at least one substantially pure lipid A-type compound of formula (I):

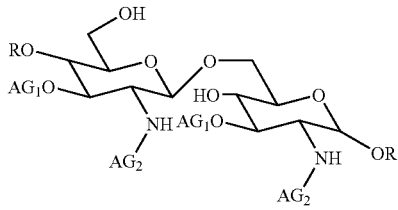

in which:
AG$_1$ denotes a 3-hydroxydecanoyl group,
AG$_2$ denotes a 3-dodecanoyloxydecanoyl group,
R independently denotes a hydrogen atom or a group PO(OR')$_2$, and
R' independently denotes a hydrogen atom, a saturated or unsaturated, linear or branched C$_1$-C$_6$ alkyl group, or a phenyl or benzyl group,
the following salts thereof when at least one R denotes a group PO(OH)$_2$: inorganic salts,
primary, secondary and tertiary amine salts, and
phosphoethanolamine salts,
and mixtures thereof.

2. The method according to claim 1, wherein the compound is an amine salt selected from the group consisting of mono-, di- and triethanolamine salts, mono-, di- or triisopropanolamine salts, 2-amino-2-methyl-1-propanol, 2-amino-2-methyl-1,3-propanediol, tris(hydroxymethyl)aminomethane, and mixtures thereof.

3. The method according to claim 1, wherein the compound is an inorganic salt selected from the group consisting of sodium, magnesium, potassium, zinc and calcium salts and mixtures thereof.

4. The method according to claim 1, wherein the isolated lipid A-type compound of formula (I) is in a composition comprising a cosmetically acceptable medium.

5. The method according to claim 4, wherein the composition comprises from 0.01 to 0.1% by weight of the at least one compound, relative to the total weight of the composition.

6. The method according to claim 4, wherein the composition further comprise at least one UV-screening agent.

7. The method according to claim 1, wherein R is PO(OR')$_2$.

8. A method to protect the skin against the damaging effects of UV radiation, the method comprising applying to skin in need thereof an effective amount of at least one isolated lipid A-type compound of formula (I):

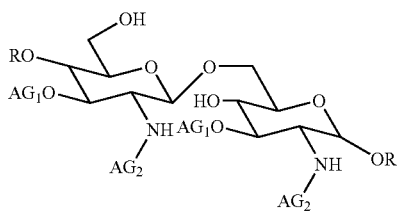

in which:
AG$_1$ denotes a 3-hydroxydecanoyl group,
AG$_2$ denotes a 3-dodecanoyloxydecanoyl group,
R independently denotes a hydrogen atom or a group PO(OR')$_2$, and
R' independently denotes a hydrogen atom, a saturated or unsaturated, linear or branched C$_1$-C$_6$ alkyl group, or a phenyl or benzyl group,
the following salts thereof when at least one R denotes a group PO(OH)$_2$: inorganic salts,
primary, secondary and tertiary amine salts, and
phosphoethanolamine salts,
and mixtures thereof; and wherein the compound is not covalently linked to another compound and does not form a lipopolysaccharide.

9. The method according to claim 8, wherein the compound is an amine salt selected from the group consisting of mono-, di- and triethanolamine salts, mono-, di- or triisopropanolamine salts, 2-amino-2-methyl-1-propanol, 2-amino-2-methyl-1,3-propanediol, tris(hydroxymethyl)aminomethane, and mixtures thereof.

10. The method according to claim 8, wherein the compound is a salt selected from the group consisting of sodium, magnesium, potassium, zinc and calcium salts and mixtures thereof.

11. The method according to claim 8, wherein the isolated lipid A-type compound of formula (I) is in a composition comprising a cosmetically acceptable medium.

* * * * *